United States Patent [19]

Percarpio

[11] 4,111,326
[45] Sep. 5, 1978

[54] CLOSURE FOR AIR EVACUATED CONTAINER

[75] Inventor: Edward P. Percarpio, North Haledon, N.J.

[73] Assignee: Becton, Dickinson and Company, Rutherford, N.J.

[21] Appl. No.: 729,643

[22] Filed: Oct. 5, 1976

Related U.S. Application Data

[63] Continuation-in-part of Ser. No. 663,921, Mar. 4, 1976, abandoned.

[51] Int. Cl.$^2$ .............................................. B65D 47/36
[52] U.S. Cl. .................................. 215/247; 215/270; 215/358
[58] Field of Search ............... 215/247, 248, 249, 260, 215/270, 271, 355, 358, DIG. 3

[56] References Cited

U.S. PATENT DOCUMENTS

| 2,186,888 | 1/1940  | Tullar .................................. 215/248 |
| 2,746,632 | 5/1956  | Bramming ............................ 215/270 |
| 3,109,549 | 11/1963 | Conklin ............................. 215/358 X |
| 3,136,440 | 6/1964  | Krug .................................. 215/247 |
| 3,189,210 | 6/1965  | Heisler .............................. 215/260 |
| 3,760,969 | 9/1973  | Shimamoto ......................... 215/247 |

FOREIGN PATENT DOCUMENTS

| 1,033,782 | 4/1953 | France ................................ 215/358 |
| 529,635   | 6/1955 | Italy .................................. 215/247 |
| 80,635    | 6/1934 | Sweden .............................. 215/247 |

Primary Examiner—Donald F. Norton
Attorney, Agent, or Firm—Kane, Dalsimer, Kane, Sullivan and Kurucz

[57] ABSTRACT

The disclosure is of a novel closure for air evacuated tubular containers and comprises a tubular body having flexible, elastic sidewalls, an open end, a closed end formed by a cannula-pierceable, flexible, elastic end wall having a concavo-convex configuration in cross-section and a flange disposed radially about the periphery of the open end. The novel closure structure takes advantage of the vacuum force in the container to maintain a gas-proof, hermetic seal, reduces the thickness required of the closure to maintain the hermetic seal and is easier to assemble in an air evacuated container. The disclosure is also of a novel method of assembling the closure of the invention in an air evacuated tubular container.

7 Claims, 16 Drawing Figures

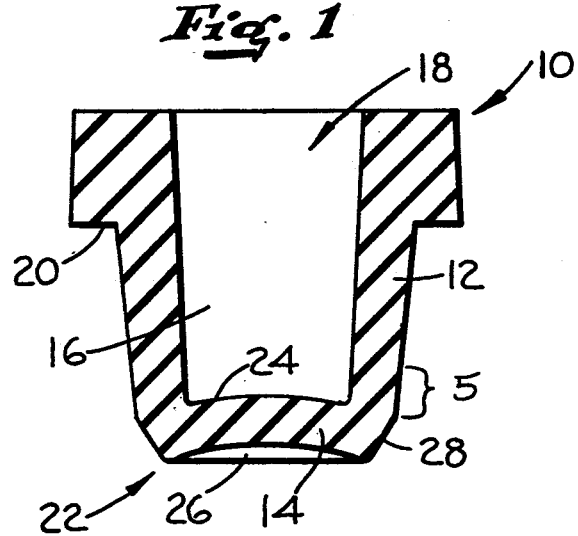
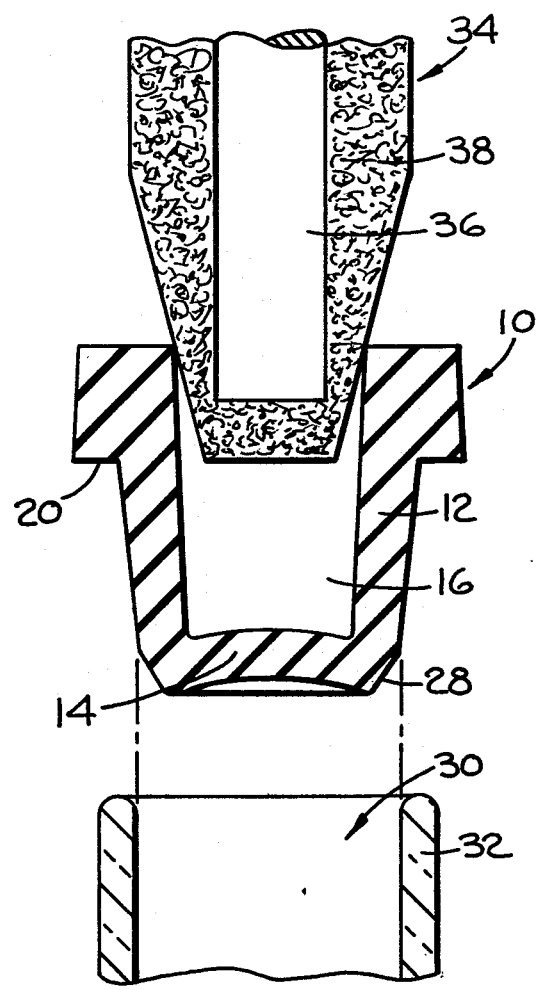
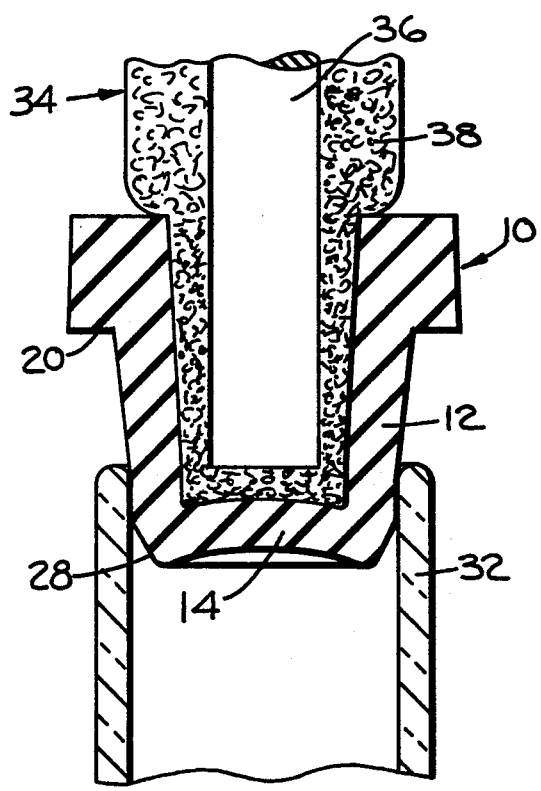
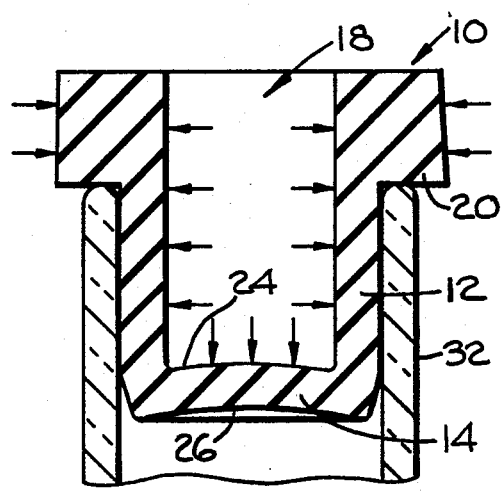

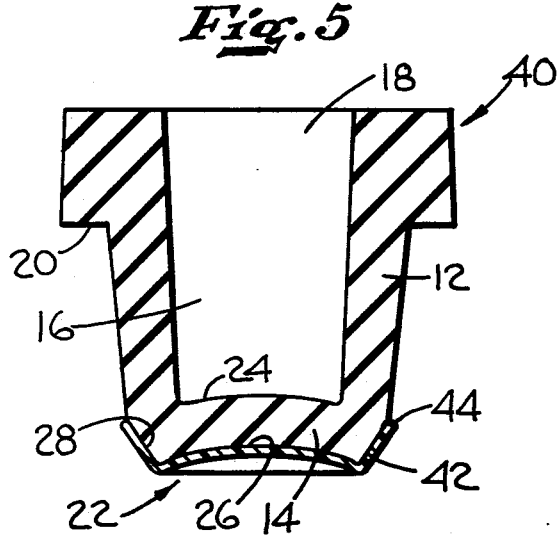
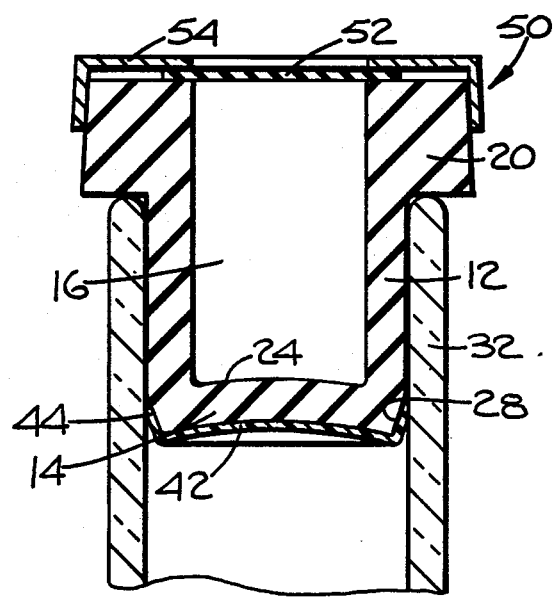
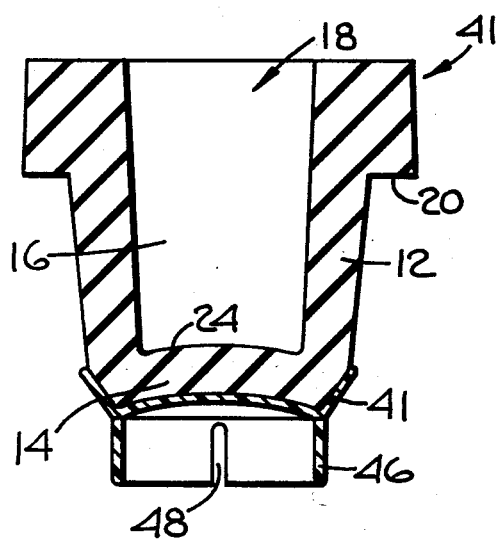
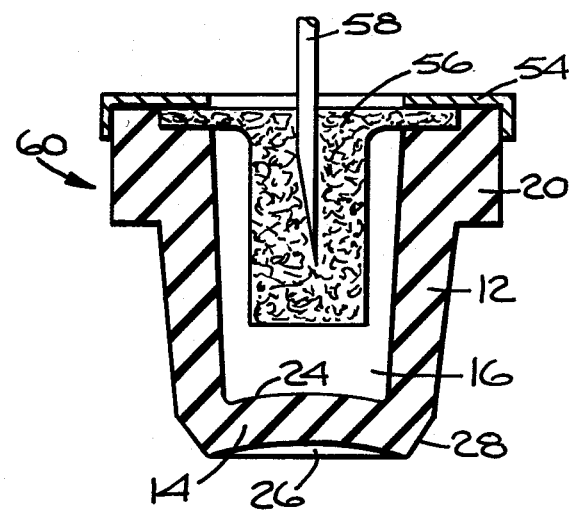

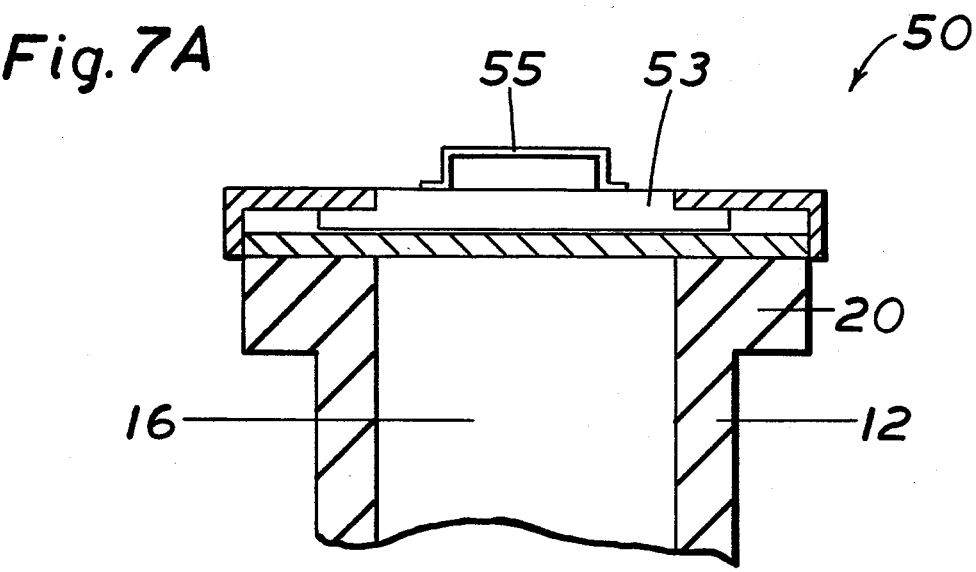
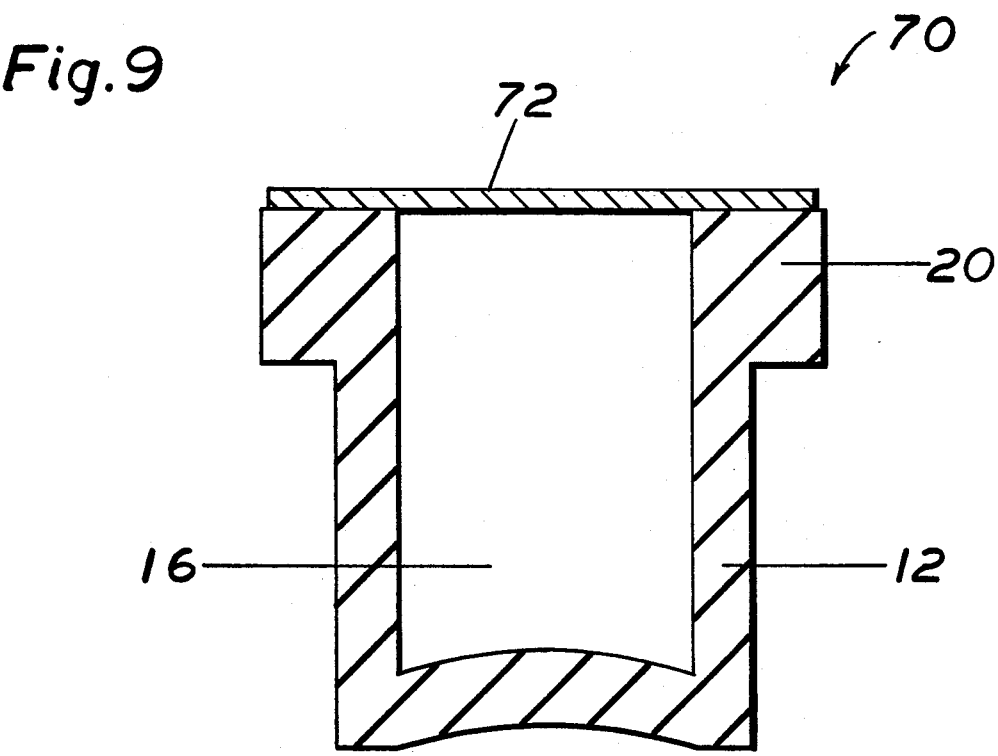

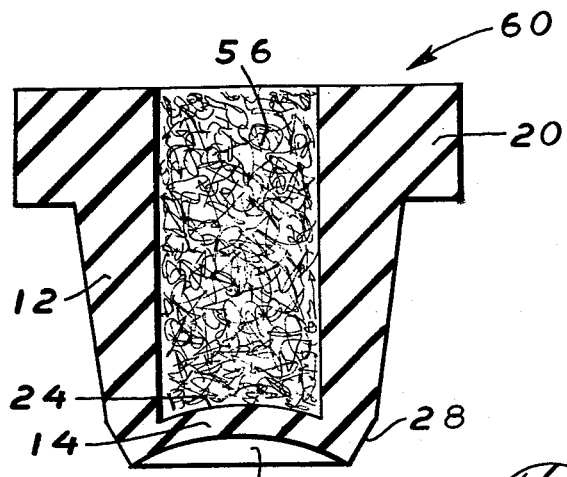
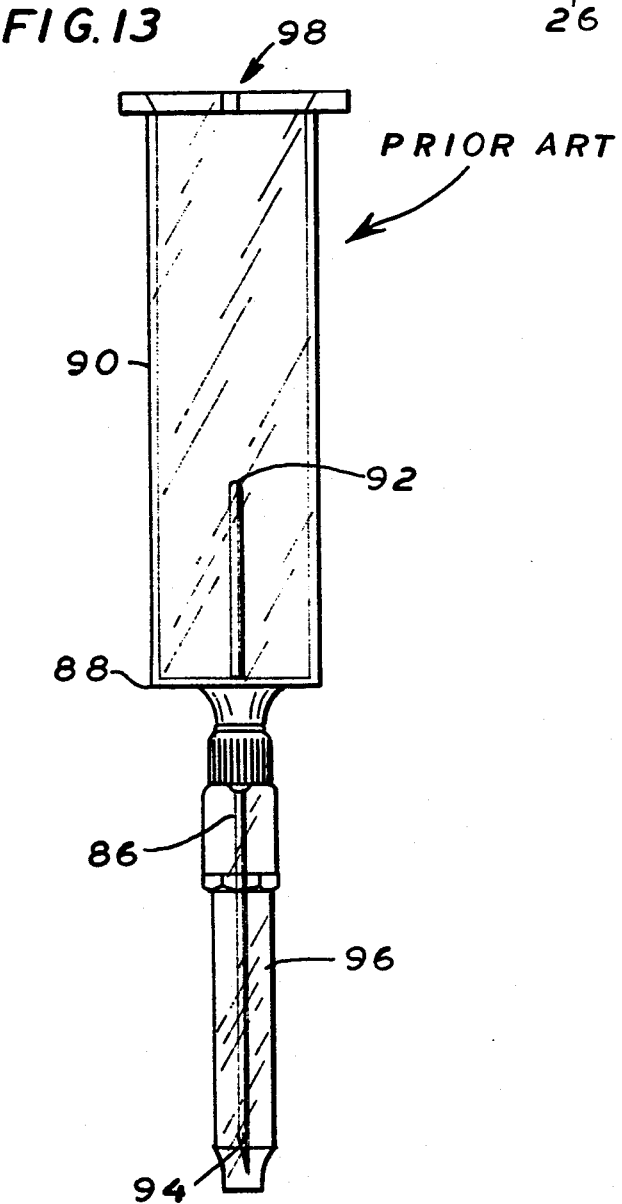
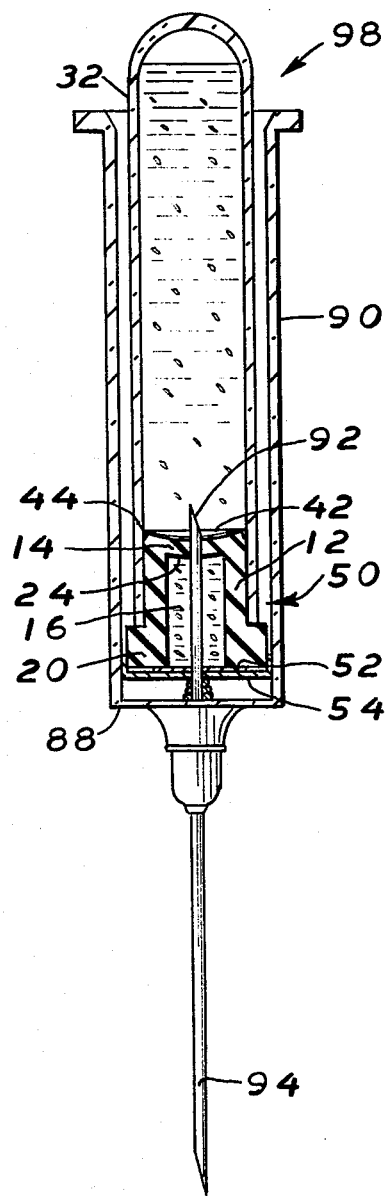

CLOSURE FOR AIR EVACUATED CONTAINER

CROSS-REFERENCE TO RELATED APPLICATION

This is a continuation-in-part of U.S. application Ser. No. 663,921 filed Mar. 4, 1976 and now abandoned.

BACKGROUND OF THE INVENTION

1. Field of the Invention

The invention concerns closures for containers and more particularly concerns gas-proof, cannula penetrable, self-sealing closures for tubular vacuum holding containers.

2. Brief Description of the Prior Art

The prior art is replete with descriptions of closure members for containers including air evacuated vacuum holding containers; see for example U.S. Pat. Nos. 2,334,905; 3,106,206; 3,136,440; 3,313,439; 3,330,282; 3,460,702; and 3,653,528.

In spite of the highly developed state of the art, closure members for air evacuated containers have many inadequate features and the perfect closure has yet to be developed. For example, in the medical, biological and laboratory fields, sealed vacuum holding tubular containers are frequently provided having cannula pierceable, self-sealing, elastomeric, gas-proof closures whereby entry into the container may be obtained by means of a needle so that fluids may be inserted or withdrawn without breaking the sterility of the container. After the needle is removed from the closure, the closure immediately reseals the pierced entry. One type of closure member frequently used with air evacuated containers is an elastomeric plug having an enlarged head portion and recesses in upper and lower portions to provide a cannula penetrable zone; see for example FIG. 4 of U.S. Pat. Nos. 3,136,440 and 3,106,206. In general, the prior art closure members for vacuum holding tubular containers are relatively thick, relatively inflexible and require relatively high forces for insertion in the open end of an air evacuated tubular container.

The closure member of my invention is an improvement over the prior art closures in that it requires less material (about 30% by weight less) for construction, without a sacrifice of gas-proofing or vacuum holding capacity. Having less bulk and lighter construction, the closure member of my invention is less costly to produce, is easier to assemble in the air evacuated container and requires a much lower force to penetrate with a needle. The latter is particularly advantageous to a more efficient utilization of the container assembly by the consumer.

The structure of my novel closure member also provides for a novel method of inserting an elastomeric closure into an air evacuated tubular container. Prior hereto, such assembly has required considerable force to make the insertion. By the method of my invention, less force is required to insert and assemble the closure member of an air evacuated tubular container. This of course is advantageous in that there is less hazard and a reduction in breakage.

SUMMARY OF THE INVENTION

The invention comprises a cannula pierceable, self-sealing gas-proof closure for sealing an open end of a tube adapted to be air evacuated, which comprises; (a) a tubular body having (1) flexible, elastic sidewalls; (2) an open first end; and (3) a closed second end formed by a cannula pierceable, flexible, elastic end wall integral with said sidewalls; and (b) a flange disposed radially about the periphery of said sidewalls adjacent to said first end; said end wall having a convex inner surface and a concave outer surface when pressure on inner and on outer surfaces is equal.

The invention also comprises a method of inserting a cannula pierceable, self-sealing, gas-proof closure into an air evacuated tubular container, which comprises; (a) providing a tubular container having an open end; (b) providing a closure member which comprises, (1) a tubular body having flexible, elastic sidewalls, an open first end and a closed second end formed by a cannula pierceable, flexible, elastic end wall integral with said sidewalls and (2) a flange disposed radially about the periphery of said sidewalls adjacent to said first end; said end wall having a convex inner surface and a concave outer surface when pressure on the inner surface equals the pressure on the outer surface; said closure member being of a dimension adapted to mate with the open end of said tubular container so that said sidewalls form a gas tight frictional engagement therewith when inserted therein; (c) providing an insertion tool which comprises a stiff elongated member having a member first end and a member second end, said member first end being enclosed by a layer of a resilient material, said member first end and enclosing layer together forming an insert end of a dimension such that when inserted into the open first end of said closure member a frictional attachment is effected between said insert end and said closure member; (d) inserting said insert end of said insert tool into the open first end of said closure member so that the bore defined by the sidewalls and end wall of said closure member is substantially filled by said insert end and the insert end of said insert tool is attached to said closure member; (e) evacuating air from said tubular container; (f) inserting the attached closure member into the open end of said closure member; and (g) withdrawing the insertion tool from its attachment with said closure member.

BRIEF DESCRIPTION OF THE DRAWINGS

FIG. 1 is a cross-sectional side elevation of an embodiment closure of the invention.

FIG. 2 is a cross-sectional side elevation of the embodiment of FIG. 1 shown with insertion apparatus prior to insertion in an open end of a tube container (the latter seen in fragmentary part).

FIG. 3 is a view as in FIG. 2 but at the start of insertion of the closure member into the open end of the tube container.

FIG. 4 is a cross-sectional side elevation of the closure embodiment of FIG. 1 but seen after complete insertion in the end of a tubular container.

FIG. 5 is a cross-sectional side elevation of a preferred closure embodiment of the invention.

FIG. 6 is a cross-sectional side elevation of another embodiment closure of the invention.

FIG. 7 is a cross-sectional side elevation of still another embodiment closure of the invention shown mounted in the end of a tubular container (the latter seen only in part).

FIG. 7A is a fragmentary view of the embodiment closure of FIG. 7 showing a protective disc component added.

FIG. 8 is a cross-sectional side elevation of yet another embodiment closure of the invention shown partially penetrated with a cannula.

FIG. 9 is a cross-sectional side elevation of another embodiment closure of the invention.

FIG. 12 is a cross-sectional side elevation of another embodiment closure of the invention.

FIG. 13 is an isometric view of a prior art tube holder.

FIG. 15 is a view as seen in FIG. 14 but after a blood collection.

DETAILED DESCRIPTION OF THE PREFERRED EMBODIMENTS OF THE INVENTION

Figure 10:
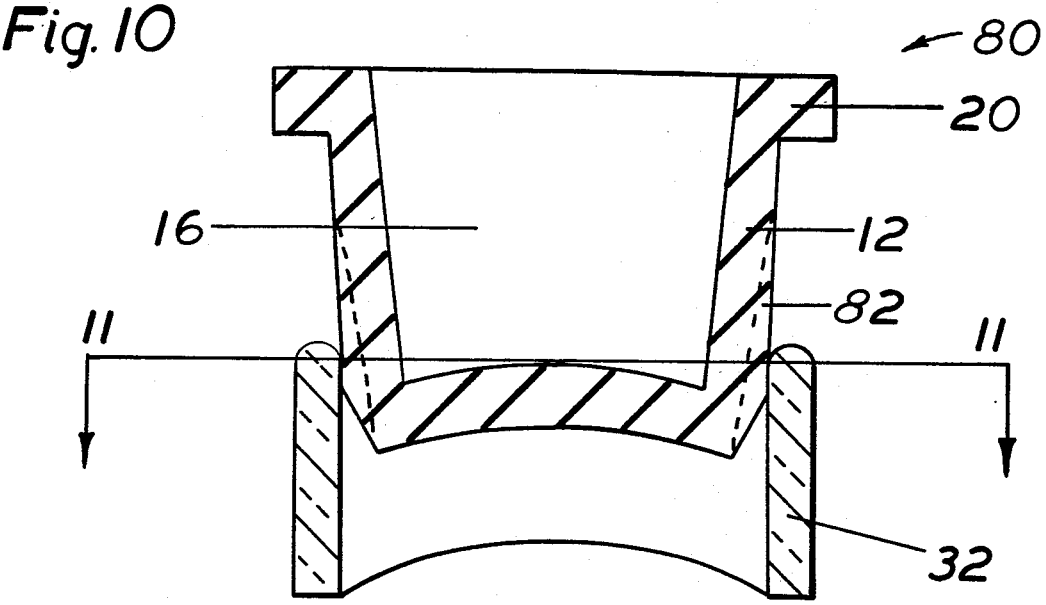
FIG. 10 is a cross-sectional side elevation of still another embodiment closure of the invention shown upon initial insertion in a vacuum container.
Figure 11:
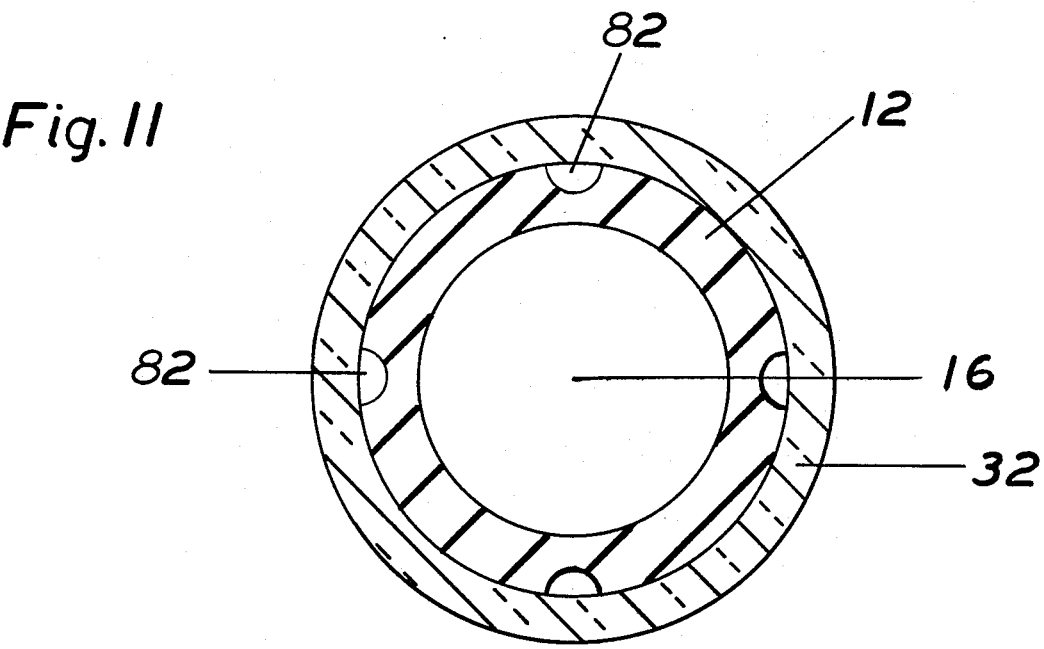
FIG. 11 is a cross-sectional view along lines 11—11 of FIG. 10.

A complete understanding of the invention may be readily obtained by a description of the preferred embodiments when read in conjunction with the accompanying drawings of FIGS. 1–15, inclusive.

Referring first to FIG. 1, a cross-sectional side elevation of an embodiment closure of the invention there is seen closure 10 which consists of a tubular body formed of flexible elastic sidewalls 12 and end wall 14 which together define bore 16 which communicates to the atmosphere through open end 18. Disposed radially about sidewalls 12 and adjacent to the open end 18 and integral therewith is a thickened portion serving as flange 20. Flange 20 serves to limit the insertion of closure 10 into an air evacuated tubular container as will be described hereinafter in greater detail. Essential to closure 10 is the concavo-convex end wall 14 closing end 22. More specifically, end wall 14 as seen in cross-section has a convex inner surface 24 and a concave outer surface 26. Inner surface 24 and outer surface 26 together with wall 14 describe a portion of a sphere or a dome. As shown in FIG. 1, the embodiment closure 10 has a bevel 28 on the sidewalls 12 at closed end 22, directed toward closed end 22. The bevel 28 facilitates assembly of the closure 10 in an air evacuated tubular container as will be described more fully hereinafter.

The closure 10 is a unitary one piece device molded of any flexible, elastomeric material conventionally used for fabricating gas-proof closures. Representative of such materials are natural rubber (cis-1,4-polyisoprene, molecular weight 100,000 to 1,000,000), polyurethane elastomers, butyl rubber (copolymers of isobutylene and diolefins) and the like. Preferred elastomeric materials are those of low gas permeability such as butyl rubbers having a Shore A hardness of circa 35 to 80.

The dimensions of closure 10 may vary widely according to the dimension of the opening to be sealed in the vacuum holding container. The diameter of the tubular body, in the zone 5 just beyond the bevel 28 (see FIG. 1), of closure 10 should be slightly larger than the inside diameter of the tubular container to be sealed so that the body portion is under compression when inserted into the tubular container. The diameter of the tubular body above the bevel 28 may increase with proximity to the flange 20 so that the tubular body above bevel 28 tapers or flares outwardly towards flange 20. In general, the thickness of the sidewalls 12 and end wall 14 is considerably less than the dimensions of prior art closures for like openings. The thickness of sidewalls 12 and end wall 14 should be such that they remain highly flexible but bear structural integrity. As an example of dimensions which may be employed in a closure 10 having a height of about 0.612 inches and an average diameter (exclusive of flange 20) of about 0.487 inches, sidewall 12 may have a thickness of about 0.909 inches. In this instance, end wall 14 may have a thickness of about 0.040 to 0.090 inches. Those skilled in the art will appreciate the significance and advantages of these very thin structural walls, in comparison to prior art closures used for the same purpose and which were heretofore not possible. As shown in FIG. 1, the embodiment closure 10 has a flange height of about 0.187 inches and a thickness through the flange area of about 0.143 inches. The bevel 28 preferably is at an angle of about 60° to the plane normal to the longitudinal axis of closure 10. A closure 10 of the above dimensions will have a weight saving over the bulkier prior art closures of similar size, of about 30%. The relatively thin wall construction of the closure 10 is less costly in terms of material cost and permits easier insertion in a vacuum container. The latter advantage results from the easier deformation of the closure 10 during insertion, requiring less force for insertion. In use, the closure 10 may be pierced by a needle or cannula thrust through the self-sealing end wall 14 when access to the enclosed area beneath the closure, mounted in a tubular container, is desired. Upon withdrawal of the needle or cannula, the self-sealing wall 14 closes the entry point to maintain enclosure.

The method of the invention is carried out by providing a closure of the invention such as closure 10, a tubular container having an open end and an insertion tool of specific structure. Referring now to FIG. 2, a cross-sectional side elevation of the embodiment closure 10 about to be inserted in the open end 30 of a tubular container 32 (seen in part), there is seen insertion tool 34 partially inserted in bore 16 of closure 10 so as to frictionally engage and hold closure 10. Insertion tool 34 comprises an elongate rigid member 36 which may be for example a rod of metal or rigid plastic resin. Member 36 should be stiff enough to withstand a force along its axis of at least 10 lbs., without bending. One end of the member 36 may be a handle (not shown) for manual operation or for attachment to the piston of an automatic ram set machine for automatic insertion of closure members. The other end of member 36 is enclosed by a layer of a resilient material 38 which is compressible. Resilient material 38 may be, for example, a foam rubber, a flexible synthetic resin foam or the like. Preferably, the resilient compressible material 38 will have a durometer hardness of circa 30. The resilient material 38 and member 36 together comprise an insert end or "finger" for handling and holding the closure 10 and directing its insertion in the open end 30 of tubular container 32. Bevel 28 aids in directing the insertion. The closure 10 is inserted under force of tool 34 in a vacuum chamber (not shown) so as to air evacuate tube container 32 prior to insertion. During initial stages of insertion, elongate member 36 carries the resilient compressible layer 38 into the bore 16 of closure 10 so as to substantially fill bore 16 and so as to give support to sidewalls 12 and end wall 14 during the insertion process (see FIG. 3). Those skilled in the art will appreciate that the tool 34 need not be constructed so compressible layer 38 fills bore 16 of the closure 10 to be inserted in a tube 32. To facilitate insertion of the tool 34 into bore 16 it may be preferable to use a relatively small section of compressible material 38 so that only a portion of the bore 16 is filled with compressible material 38. In FIG. 3, initial insertion of closure 10 has been effected. Due to the fact that sidewalls 12 are relatively thin and flexible and insert end layer 38 is readily compressed, the closure is easily inserted in an air evacuated tube container 32 with a minimum of required force. The sidewalls 12 will flex inwardly vary easily to overcome the resistance of insertion into the smaller diameter tube 32. After complete insertion up to flange 20, the insertion tool 34 is easily removed leaving the closure 10 in place as shown in FIG. 4, a cross-sectional side elevation of the closure 10 mounted to hermetically seal air evacuated tube container 32. The closure 10, thus mounted, will sustain and hold the vacuum in container 32 even though closure 10 have relatively thin, flexible sidewalls 12 and end wall 14 because of the concavo-convex configuration of end wall 14 in conjunction with the relatively flexible sidewalls 12.

More specifically, and as illustrated by the arrows in FIG. 4, the pressure differential (atmosphere to tube vacuum) helps create a tighter seal between closure 10 and tube 32 than can be accomplished by simple compressive force alone as is the case with prior art closures. In addition to pressure differential forces which help seal and hold the closure in place, there exists a new radial force not present in prior art closures. The radial force is induced by the radial outward motion from the center of wall 14 along the axis of end wall 14 to the periphery thereof. This outward force results from the higher pressure on the upper surface 24 of end wall 14 as compared to the lower pressure (vacuum) exerting itself upon lower surface 26. The pressure differential flexes end wall 14 to flatten the concavo-convex configuration thereby creating the radial force directed toward the periphery of end wall 14. Since the force is concentrated in the lower solid portion of the closure, in the area of end wall 14, a powerful restraining and sealing force against tube 32 is obtained due to the flexibility of sidewalls 12. This additional sealing force not found in prior art closures enhances the hermetic seal between closure and container. In the absence of the concavo-convex configuration of end wall 14, the sidewall 12 would actually pull away from the walls of container 32 and closure 10 would be drawn into the container 32 by the vacuum force. The long term preservation of vacuum in container 32 is also enhanced and rendered more positive since stress relaxation of the elastomeric material (compression set) is not a factor in obtaining the hermetic seal obtained with use of closure 10. The radial sealing force also provides increased resistance to accidental removal of closure 10 during needle withdrawal after use as will be described in greater detail hereinafter.

A further advantage in the closure member 10 of the invention resides in the visual indication it provides as to the state of the vacuum maintained in tubular container 32. As described above, the pressure differential on surfaces 24 and 26 of end wall 14 causes a flattening out of the concavo-convex configuration of end wall 14. If there is a loss of vacuum in the container 32, the natural arc of the concavo-convex configuration will return with the equalization of pressures on surfaces 24 and 26. This return of an arc is observable and an indication to personnel that vacuum has been lost in container 32. Those skilled in the art will appreciate many refinements possible to determine the degree of vacuum loss, i.e.; simple measurement of bore 16 depth, or mechanical and optical means of measurement of the convex arc are possible.

Referring now to FIG. 5, a cross-sectional side elevation of a preferred closure of the invention, there is seen closure 40 which is essentially the same structure found in closure 10 of FIG. 1 but with the addition of a protective cap 42 adhesively attached to end 22 so as to cover the outer surface 26 of end wall 14 and bevel 18 surface. Cap 42 isolates closure 40 from the contents of the container in which it is emplaced, obviating the possibility of any interaction between the container contents and the closure 40. For example, if the container 32 is to be employed in the collection of blood, additives such as oxalates or citrates, conventionally added to such containers, are prevented from clinging to the elastomeric closure 40 by the interposition of protective cap 42. Protective cap 42 is preferably of a synthetic thermoplastic resin material which is stable when sterilized by wet or dry heat. Representative of such materials are polypropylene, high density polyethylene, polytetrafluoroethylene and the like. Preferred as the material for fabricating cap 42 is polytetrafluoroethylene because of its extremely high cold flow properties and its resistance to attachment of fibrin or red blood cells which might otherwise attach to the closure 10 when the container is to hold blood specimens. It is important that the cap 42 be firmly secured to the end wall 14 so as not to separate therefrom and be loosely deposited in the vacuum holding container. In the closure 40, a polytetrafluoroethylene cap 42 having a thickness of circa 0.015 inches makes contact with the inner walls of the container to be closed, along its peripheral edges 44. When closure 40 is mounted in the opening of an air evacuated tubular container, the edges 44 of cap 42 are forced against the inside container tubular walls by virtue of the action of the domed end wall 14 as described above. This results in a very high sealing pressure. It is important to note that peripheral edges 44 do not interrupt a substantial surface contact between the sidewalls 12 and the interior walls of the tubular container in which closure 40 will be mounted. The substantial elastomer-container contact offers primary resistance to accidental fallout of the closure 40, providing tight frictional engagement of the closure 40 with the container. The high sealing pressure coupled with the high cold flow property of polytetrafluoroethylene creates an intimate and absolute seal enhancing the hermetic seal of the closure 40 and isolating the elastomeric material of closure 40 from contacting the container contents. In addition, as previously described, the new radial force found in the closures of the invention caused by differential pressure, provides for a new radial sealing force caused by the radial "rolling" action of the disc 42 edge 44 against the inner wall of the container in which the closure 40 is mounted. This provides for a very secure, liquid seal while not interfering with the hermetic seal formed by the elastomer body sidewalls 12 with the container body.

Referring now to FIG. 6, a cross-sectional side elevation of an alternate embodiment enclosure of the invention, there is seen a closure 41 which differs from closure 40 in FIG. 5 only in respect to the structure of end cap 41. End cap 41 as seen in FIG. 6 may be fabricated from the same materials employed in the fabrication of end cap 42. End cap 41 differs in that it has a skirt portion 46 which is of a dimension adapted to permit nesting in the open end of a tubular container prior to insertion of the closure member 41 therein. Skirt portion 46 which is integrally molded with cap 41 is a convenience in assembling closure 41 into the open end of an air evacuated container. The skirt 46 is of a dimension slightly less than the internal diameter of the tubular container so that closure 41 may be set up initially on the mouth or orifice of the container and later inserted as described above, i.e.; with the aid of an insertion tool 34. In a preferred embodiment, skirt 46 will have one or more slots 48 therein to facilitate the air evacuation from the tubular container after the closure 41 is set on the mouth of the tubular container but before insertion therein.

As shown in FIG. 1, a cross-sectional side elevation of a further embodiment closure of the invention, there is seen a closure 50 which is, essentially, a closure 40 as described above and shown in FIG. 5 but with an added puncture diaphragm 52 secured (preferably bonded) to the flange 20 by a relatively stiff ring 54. The ring 54 may be a metal or plastic ring and contacts only the closure 50. The ring 54 also supports and stiffens the puncture diaphragm 52. Diaphragm 52 covers and seals bore 16 closed to prevent the collection of contaminants therein such as dirt, dust, foreign objects and the like which might be carried through the pierceable end wall 14 upon puncture with a cannula or needle. The puncture diaphragm 52 also serves to wipe a cannula or needle upon withdrawal, thereby wiping any droplets of fluids from the needle. This is particularly advantageous when the fluid concerned may be hazardous to operating personnel. The wiped drop or droplets of material fluids are retained in bore 16 upon withdrawal of the cannula through puncture diaphragm 52.

Figure 14:
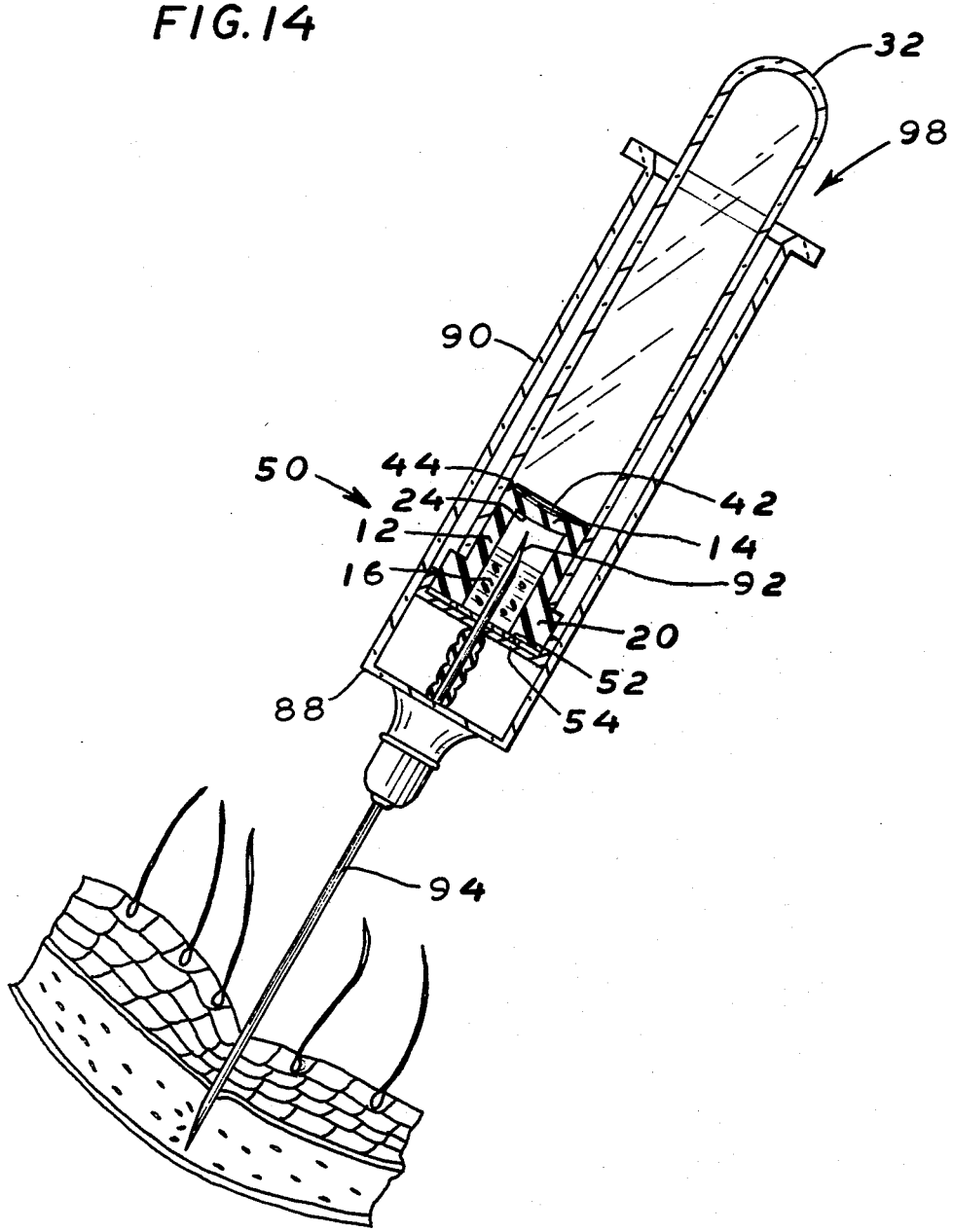
FIG. 14 is a cross-sectional side elevation of a blood collecting container employing a closure of the invention, mounted in the holder of FIG. 13 and initially inserted in a blood vessel.

FIG. 7 also shows the close hermetic seal effected between protective cap 42 at end 44 with the interior wall of tubular container 32. As described above, the vacuum within container 32 in conjunction with the atmospheric pressure upon surface 24 of end wall 14 causes the concavo-convex configuration to flatten out and force protective cap ends 44 (lining the bevel 28) with very high pressure against the tubular container 32 walls. Those skilled in the art will also appreciate that the relatively thin concavo-convex end wall 14 facilitates needle penetration when access to the contents or space of container 32 is desired. Not only is the end wall 14 relatively thin in comparison to prior art closures for hermetically sealing tubular containers, but the concavo-convex configuration in conjunction with the fact that it is under stress when mounted in a vacuum holding container 32, causes greater crack growth upon penetration with a needle, allowing for easier penetration. The radial force exerted by the concavo-convex configuration of end wall 14 also secures the closure 10 in place during withdrawal of the needle. The diaphragm 52 shown in FIG. 7 also functions to position and hold a veni-puncture needle prior to its piercing the end wall 14. FIG. 13 shows a conventional veni-puncture needle and holder of the prior art. The assembly comprises a double ended piercing cannula 86 mounted in the closed end 88 of a tubular holder 90 so that needle end 92 is centered within holder 90 and needle end 94 is outside of holder 90 and encased by sheath 96. In initial use, a tubular container 32 closed by a closure 50 is inserted in the open end 98 of holder 90 and seated on the needle end 92 by needle end 92 piercing the diaphragm 52 as shown in FIG. 14. FIG. 14 shows the needle end 92 resting in bore 16 and the still closed vacuum container 32 held in its position by the frictional forces between needle 86 and diaphragm 52. With container 32 thusly secured, the operator may unsheath needle end 94 and use that end to accomplish a veni-puncture. A shown in FIG. 14, the initial blood flow upon veni-puncture is into bore 16. The operator, when ready to collect a blood specimen in container 32 then moves the container 32 further into holder 90 so needle end 92 will pierce end wall 14 and enter the vacuum chamber of container 32 as shown in FIG. 15. When the desired amount of blood has been collected in container 32 as shown in FIG. 15, the veni-puncture is closed by withdrawal of needle end 94 and container 32 may then be withdrawn from holder 90 to seal the blood specimen collected in container 32. The initial blood flow received in bore 16 is also sealed by the self-sealing diaphragm 52 which also functions to wipe the needle point 92 free of any residual blood droplets as it is withdrawn through the diaphragm 52. This sealing of bore 16 and wiping of needle point 92 assures that blood is not spilled into the vicinity of the operator or the patient. This is particularly valuable if the blood is or poses a health hazard by open spilling into the environment.

An advantage of the above described procedure is that it frees the operator from having to juggle a loose collection container and/or spill blood unnecessarily in the vicinity of the patient while collecting a specimen.

FIG. 7A is a cross-sectional side elevation of a fragment of closure 50 as shown in FIG. 7 with the addition of a removable disc 53 held in place over diaphragm 52 by ring 54. The removable disc 53 serves to preserve the sterile condition of a diaphragm 52 and surface 24 prior to needle insertion. Alternatively, the removable disc 53 may be used without a puncture diaphragm 52 to protect bore 16 and surface 24 from contamination prior to insertion of a needle through the closure 10. The disc 53 may be stripped off prior to use by pulling the tearable finger gripping surface 55.

Referring now to FIG. 8, there is seen a cross-sectional side elevation of another embodiment closure 60 of the invention. Closure 60 is essentially a closure as seen in FIG. 7 but without protective cap 42 and with a different puncture diaphragm member. In closure 60 of FIG. 8, the puncture diaphragm 56 consists of a cylinder of absorbent material such as a polyurethane foam. The closure 60 is advantageous in halting the flow of materials through needle 58 after it has been withdrawn from a tubular container (in which closure 60 is mounted) or prior to insertion through end wall 14 (but after veni-puncture) to prevent premature blood transfer. More specifically, needle 58 is initially thrust through puncture diaphragm 56, through bore 16, through end wall 14 and into the vacuum space of the tubular container (not shown in FIG. 8). The cannula thus entered may bear fluids into the vacuum holding container. Upon withdrawal of the cannula 58, it may be positioned so that its end terminates in puncture diaphragm 56. Puncture diaphragm 56 being an absorbent material will stem continued flow of fluids through needle 58 until such time as the other end may be disconnected from the fluid source.

Referring now to FIG. 12, a cross-sectional side elevation of a preferred closure 60 is seen, with analagous parts numbered as in FIG. 8. The closure of FIG. 12 differs from that of FIG. 8 in that the diaphragm 56 fills bore 16, obviating the need for ring 54. The diaphragm 56 is advantageously flexible so as not to interfere with the action of endwall 14 as previously described.

FIG. 9 is a cross-sectional side elevation of another embodiment closure 70 of the invention which differs from the closure 10, 40 and 41 described above in that the bore 16 is closed and protected from contamination by a strip 72 of pressure sensitive tape of a removable sheet of a polymeric resin. The strip 72 may be peeled off when entry through the closure 70 with a cannula is desired.

FIG. 10 is a cross-sectional side elevation of still another embodiment closure 80 of the invention shown being initially inserted in a tubular container 32. The closure 80 differs from closure 10 seen in FIG. 1 in that a plurality of grooves 82 are cut in sidewalls 12, in the direction of the vertical axis of the closure 80. The grooves 82 facilitate the insertion of the closure 80 into the tube 32 by reducing the frictional force to be overcome between tube 32 and closure 80 and also allows the escape of an air remaining in tube 32 which will be displaced by the closure 80. The relationship of the grooves 82 can be seen in greater detail by referring to FIG. 11, a cross-sectional view along lines 11—11 of FIG. 10.

Those skilled in the art will appreciate that many modifications may be made to the article and the method of the invention without departing from the spirit of the invention. For example, any closure of the invention may be inserted in a tubular container with the aid of a simple metal or plastic push-rod. As a further example, the closures described above may be fabricated in any desired size. Preferably however, the diameter of the closure will bear a relationship to the height of the closure within the ratio of from about 0.8:1. This preferred ratio assures maximum sealing effect from the structure of the closures of the invention.

What is claimed:

1. A cannula-pierceable, self-sealing, gas-proof closure for sealing an open end of an air evacuated blood collection tube, which comprises;

(a) a tubular elastomeric body having
      (i) flexible, elastic sidewalls;
      (ii) an open first end; and
      (iii) a closed second end formed by a cannula pierceable, flexible, elastic end wall integral with said sidewalls; and
   (b) a flange disposed radially about the periphery of said sidewalls adjacent to said first end; said end wall having a convex inner surface and a concave outer surface when pressure on inner and on outer surfaces is equal, said tubular body having a diameter which bears a ratio to the height of the body of about 0.8:1 and to the thickness of the second end of from 5.4:1 to 12.1:1; whereby when the closure is emplaced in and sealing an open end of an air-evacuated tube, the higher pressure on the convex inner surface of the end wall as compared to the lower pressure (vacuum) exerting itself on the concave outer surface creates a pressure differential on the end wall, flexing and flattening the concavo-convex configuration and creating a radial force directed toward the periphery of the end wall, said force affecting a restraining and sealing force between the closed second end of the elastomeric body and the air-evacuated tube.

2. The closure of claim 1 wherein said tubular body is cylindrical.

3. The closure of claim 1 wherein said second end has a smaller diameter than said first end.

4. The closure of claim 3 wherein the sidewalls at said second end are bevelled toward said second end.

5. The closure of claim 1 wherein said body is fabricated from butyl rubber.

6. The closure of claim 1 wherein said flange is an integral part of said sidewalls.

7. The closure of claim 1 wherein said body is molded from an elastomeric material selected from natural rubber, polyurethane and butyl rubber.

* * * * *